US011175736B2

(12) United States Patent
Baugh et al.

(10) Patent No.: US 11,175,736 B2
(45) Date of Patent: Nov. 16, 2021

(54) APPARATUS, SYSTEMS AND METHODS FOR USING PUPILLOMETRY PARAMETERS FOR ASSISTED COMMUNICATION

(71) Applicant: South Dakota Board of Regents, Vermillion, SD (US)

(72) Inventors: Lee Baugh, Vermillion, SD (US); Kelene Fercho, Vermillion, SD (US)

(73) Assignee: South Dakota Board of Regents, Brookings, SD (US)

( * ) Notice: Subject to any disclaimer, the term of this patent is extended or adjusted under 35 U.S.C. 154(b) by 348 days.

(21) Appl. No.: 16/189,653

(22) Filed: Nov. 13, 2018

(65) Prior Publication Data

US 2019/0146580 A1 May 16, 2019

Related U.S. Application Data

(60) Provisional application No. 62/584,433, filed on Nov. 10, 2017.

(51) Int. Cl.
| | | |
|---|---|---|
| *G06F 3/01* | (2006.01) | |
| *A61B 3/14* | (2006.01) | |
| *A61B 3/11* | (2006.01) | |
| *A61B 3/00* | (2006.01) | |

(52) U.S. Cl.
CPC .............. *G06F 3/013* (2013.01); *A61B 3/111* (2013.01); *A61B 3/14* (2013.01); *G06F 3/015* (2013.01); *A61B 3/0025* (2013.01)

(58) Field of Classification Search
CPC .......... G06F 3/013; G06F 3/015; A61B 3/111; A61B 3/14; A61B 3/025

USPC .......................................................... 351/204
See application file for complete search history.

(56) References Cited

U.S. PATENT DOCUMENTS

| | | | |
|---|---|---|---|
| 5,583,795 A | 12/1996 | Smyth | |
| 8,807,753 B2 | 8/2014 | Maddess et al. | |
| 9,211,078 B2 | 12/2015 | Meggiolaro et al. | |
| 2008/0255949 A1 | 10/2008 | Genco et al. | |
| 2010/0324440 A1 | 12/2010 | Moore et al. | |
| 2014/0012509 A1 | 1/2014 | Barber | |
| 2016/0078771 A1* | 3/2016 | Zhuang | G10L 15/26 434/236 |
| 2016/0274660 A1 | 9/2016 | Publicover et al. | |
| 2016/0367165 A1 | 12/2016 | Khaderi | |
| 2017/0131768 A1 | 5/2017 | Budavari et al. | |

FOREIGN PATENT DOCUMENTS

WO   2014146168 A1   9/2014

\* cited by examiner

*Primary Examiner* — Marin Pichler
*Assistant Examiner* — Mitchell T Oestreich
(74) *Attorney, Agent, or Firm* — Dentons Davis Brown, P.C.; Matthew Warner-Blankenship

(57) ABSTRACT

The disclosed apparatus, systems and methods relate to pupillary assisted communication systems, devices and methods. A classification algorithm such as a hybrid classification algorithm is utilized to utilize at least one pupillary-response sensing device and at least one non-pupillary response sensing device to generate and process subject data to improve feedback systems and improve non-verbal communication and stimulus-response operations systems.

20 Claims, 8 Drawing Sheets

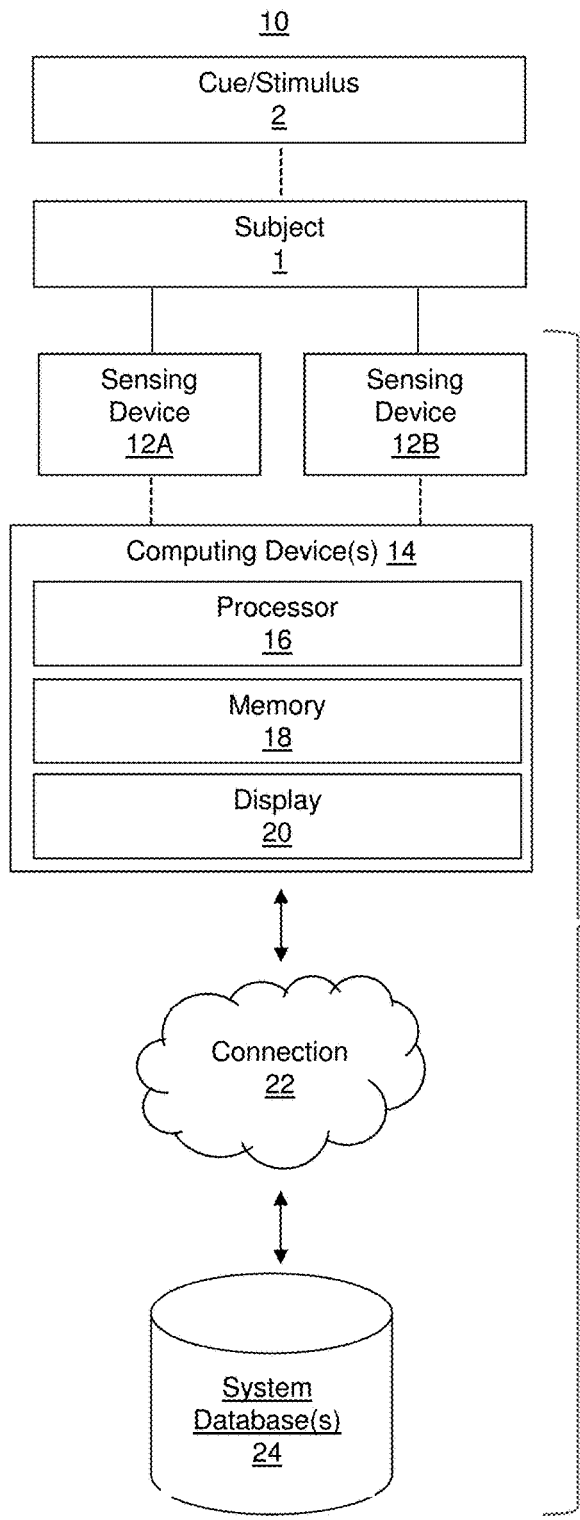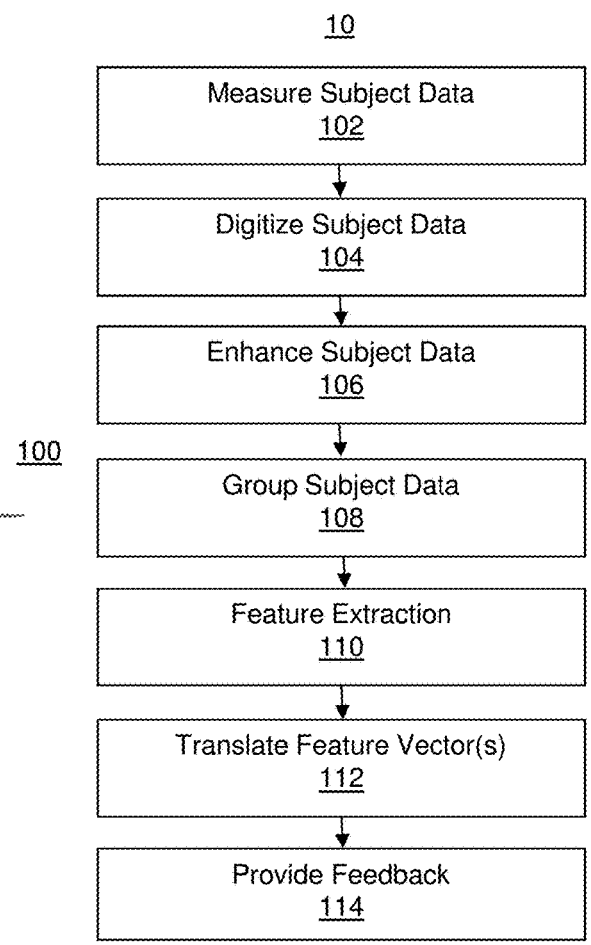
FIG 1A
FIG 1B

Table 1
P300

|  | True Positive | True Negative |
|---|---|---|
| Filter-Bank CSP | 0.40 | 0.82 |
| Common Spatial Patterns (CSP) | 0.54 | 0.67 |

Table 2
Pupil Diameter

|  | True Positive | True Negative |
|---|---|---|
| Log-Bandpower | 0.61 | 0.57 |
| Common Spatial Patterns (CSP) | 0.58 | 0.58 |

Table 3
Pupil Diameter + P300

|  | True Positive | True Negative |
|---|---|---|
| Filter-Bank CSP | 0.41 | 0.82 |
| Common Spatial Patterns (CSP) | 0.61 | 0.68 |

APPARATUS, SYSTEMS AND METHODS FOR USING PUPILLOMETRY PARAMETERS FOR ASSISTED COMMUNICATION

CROSS-REFERENCE TO RELATED APPLICATION(S)

This application claims priority to U.S. Provisional Application No. 62/584,433 filed Nov. 10, 2017 and entitled "Methods For Using Pupillometry Parameters For Assisted Communication And Related Systems." which is hereby incorporated by reference in its entirety under 35 U.S.C. § 119(e).

TECHNICAL FIELD

The disclosed technology relates generally to systems, methods, and devices for the improved selection of visually displayed targets, icons, or symbols, letters, words, or other symbols using pupillometry parameters. In certain embodiments, the disclosed technology relates to assistive technologies for the purposes of aided communication in patients who have experienced loss of verbal and/or gestural communication.

BACKGROUND

Humans process information and complete tasks using processes such as sensory and perceptual processing, attention, memory, response selection, response execution, and system or performance feedback. In some circumstances, these processes may be negatively affected by a physically or technologically limited operational environment or a physical limitation of an individual or operator. For example, when patients suffer from severe motor disorders, such as those that accompany amyotrophic lateral sclerosis (ALS), brainstem stroke, or cerebral palsy, alternative forms of communication may be required to offset the loss of verbal and gestural communication that result from a physical limitation of the person. Alternatively, in complex operational environments, such as those requiring the use of hands and/or feet like the piloting of aircraft and the playing of modern video games, additional response selections and executions can be limited due to those complex operational environments. Further, in some instances, the use of pupil dynamics such as a change in pupil size, may be useful in contexts in which a standard user interface is not practical, such as controlling a virtual reality headset.

In these contexts, response selection and execution would improve if the individual were able to make controlled inputs to the system or selections that were not gestural or verbal in nature. The disclosed systems, devices and methods are directed to enabling individuals to make response selections by detecting changes in the eye pupillary response to a visual display. In a general sense, the disclosed systems, devices and methods provide new and useful tools for use in the field of assistive communication technologies. In addition, the disclosed systems, devices and methods provide new and useful approaches for use by those who wish to improve and/or reach their optimal performance potential with respect to increasing the accuracy or rate of response selections without the need for verbal or gestural responses, such as in transportation, video gaming, controlling virtual reality headsets, and the like.

BRIEF SUMMARY

Discussed herein are various devices, systems and methods relating to the improved selection of visually displayed targets, icons, or symbols, using pupillometry parameters.

In various Examples, a system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

One Example includes an assisted communication system, including: at least one assistive communication technology device constructed and arranged to generate subject data; at least one computing device including at least one processor constructed and arranged for executing a classification algorithm including: grouping subject data into sample blocks, executing a feature extraction algorithmic step to produce at least one feature vector, translating the at least one feature vector, and providing feedback. The assisted communication system also includes an operations system constructed and arranged to communicate the feedback Other embodiments of this Example include corresponding computer systems, apparatus, and computer programs recorded on one or more computer storage devices, each configured to perform the actions of the methods.

Implementations according to this Example may include one or more of the following features. The system where the subject data includes pupillary response data and other physiological response data. The system where the subject data includes brain signal data. The system further including an EEG. The system further including a display constructed and arranged to provide the feedback. The system where at least one assistive communication technology device is constructed and arranged to measure at least one response selected from the group including of pupil size, eye gaze dwell time, eye blink and eye movement. Implementations of the described techniques may include hardware, a method or process, or computer software on a computer-accessible medium.

Another Example includes a pupillary assisted communication system, including: at least one sensing device constructed and arranged to generate subject data; b. at least one computing device including at least one processor constructed and arranged for executing a classification algorithm including: grouping subject data into sample blocks, executing a feature extraction algorithmic step to produce at least one feature vector, and translating the at least one feature vector, where the at least one sensing device includes at least one assistive communication technology device constructed and arranged to collect subject data via pupillary response. Other embodiments of this Example include corresponding computer systems, apparatus, and computer programs recorded on one or more computer storage devices, each configured to perform the actions of the methods.

Implementations according to this Example may include one or more of the following features. The system further including a non-pupillary physiological sensor. The system where the subject data includes at least one response selected from the group including of pupil size, eye gaze dwell time, eye blink, eye movement. EEG, functional near infrared spectroscopy, electrocorticographraphy, ultrasound, change in heart rate, motor evoked responses and galvanic skin responses. The system where the algorithm is a hybrid algorithm. The system where subject data is generated via BCI. The system where the subject data is generated via augmentative and alternative communication. Implementations of the described techniques in this Example may include hardware, a method or process, or computer software on a computer-accessible medium.

Another Example includes a pupillary assisted communication system, including: a pupillary-response sensing device constructed and arranged to generate subject data; a non-pupillary response sensing device constructed and arranged to generate subject data; at least one computing device including a display, memory, and at least one processor constructed and arranged for executing a hybrid classification algorithm including a plurality of steps including: grouping subject data from the pupillary-response and non-pupillary response sensing devices into sample blocks, executing a feature extraction algorithmic step to produce at least one feature vector, and translating the feature vector. Other embodiments of this Example include corresponding computer systems, apparatus, and computer programs recorded on one or more computer storage devices, each configured to perform the actions of the methods.

Implementations according to this Example may include one or more of the following features. The system where the subject data includes at least one response selected from the group including of pupil size, eye gaze dwell time, eye blink, eye movement, EEG, functional near infrared spectroscopy, electrocorticography, ultrasound, change in heart rate, motor evoked responses and galvanic skin responses. The system where subject data is generated via BCI. The system where the subject data is generated via augmentative and alternative communication. The system where the feature algorithmic step further includes a plurality of sub-steps. The system where the feature algorithmic sub-steps includes: a vector computing sub-step. The system may also include a scatter matrix computing sub-step. The system may also include an eigenvector and eigenvalue computing sub-step. The system where the feature algorithmic sub-steps includes an eigenvalue sorting step. The system where the feature algorithmic sub-steps includes a sample transforming step. Implementations of the described techniques may include hardware, a method or process, or computer software on a computer-accessible medium.

While multiple embodiments are disclosed, still other embodiments of the disclosure will become apparent to those skilled in the art from the following detailed description, which shows and describes illustrative embodiments of the disclosed apparatus, systems, and methods. As will be realized, the disclosed apparatus, systems and methods are capable of modifications in various obvious aspects, all without departing from the spirit and scope of the disclosure. Accordingly, the drawings and detailed description are to be regarded as illustrative in nature and not restrictive.

BRIEF DESCRIPTION OF THE DRAWINGS

FIG. 1A is a process view of an exemplary embodiment of the classification system described, consisting of a subject, sensing devices, computing devices, and a display system.

FIG. 1B shows the corresponding process steps utilized by the implementation exemplified in FIG. 1A.

DETAILED DESCRIPTION

Figure 1C:
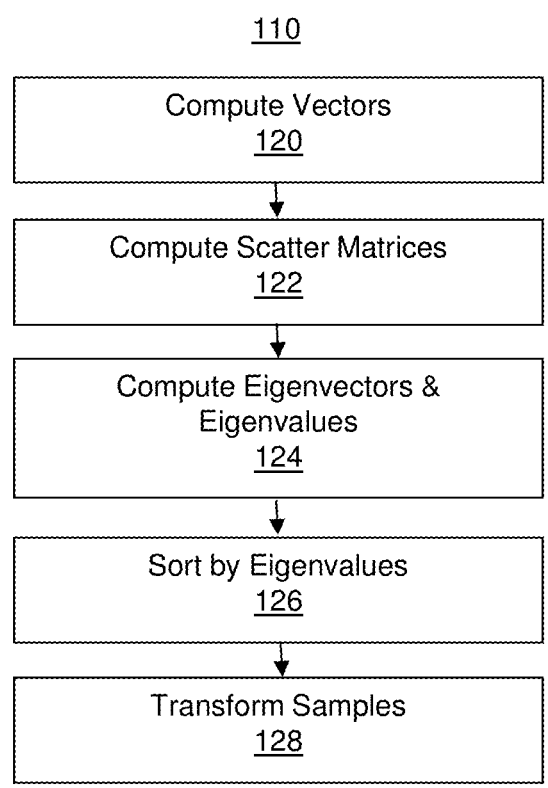
FIG. 1C is a process view of one implementation of a feature extraction algorithmic step, according to the implementation of FIG. 1B.

The various embodiments disclosed or contemplated herein relate to the use of eye pupil features, such as pupil size, as a single input or along with other physiological inputs in operational systems to enhance the performance of those operational systems. In various implementations, an assistive communication technology combines one or more physiological inputs—such as pupillary response, EEG, or any of the others described herein—using a hybrid classification algorithm to assess physiological feedback and yield improved accuracy in response to cues over known systems and methods. Additionally, in alternate implementations, eye pupil features alone, such as a change in size, may be used as a single input to a classification algorithm to identify user intent for assisted communication or other technologies. It is understood that in these implementations, the disclosed systems may be used for assisted communication by combining brain signals, or other physiological or biological signals described herein, with eye pupil features via such a hybrid classification algorithm to generate operational outputs, or by using eye pupil features as the sole input.

As shown in FIG. 1A and FIG. 1B, various implementations of the devices, systems and methods discussed herein utilize several optional components (FIG. 1A) implementing several optional steps (FIG. 1B). In certain of these implementations, and as shown in FIG. 1A, an assisted communication (AC) system 10 such as a pupillary response assisted communication system 10 comprises at least one sensing device 12 such as an assistive communication technology device 12A or physiological sensor 12B used to measure physiological response to extract and transduce subject data via a classification algorithm 100 such as a hybrid classification algorithm 100, as described in relation to FIG. 1B. It is understood that in various implementations, one assistive communication technology device 12A is constructed and arranged to measure pupillary response subject data, while another device 12B is constructed and arranged to collect other physiological subject 1 data in response to cues 2, in the case of a hybrid classification system 10 and associated classification algorithm 100.

It is understood that as discussed herein, the various physiological input sensors or devices may be referred to generally in several ways, and that while many such sensing devices such as the EEG can have a plurality of other functions in other applications, in the presently-disclosed implementations each of these is service as an assistive communication technology device.

In various implementations, the AC system 10 such as a hybrid pupillary AC system 10 may also be operatively connected directly and/or indirectly, such as over a network or wired connection, to one or more computing devices 14, that may include at least one processor 16 coupled to a system memory 18, as shown in FIG. 1A. The system memory 18 may include computer program modules and program data. As described above, the operations associated with respective computer-program instructions in the program modules could be distributed across multiple computing devices 14. A display 20 can also be provided for the depiction of output information.

The system 10 can also be in electronic communication via a connection 22 with system databases 24 (e.g., database 1, database 2, . . . , database n). Various devices may be connected to the system, including, but not limited to, medical devices, medical monitoring systems, client computing devices, consumer computing devices, provider computing devices, remote access devices, and the like. This system 10 may receive one or more inputs and/or one or more outputs from the various sensors, medical devices, computing devices, servers, databases, and the like.

In various implementations, the connection 22 may represent, for example, a hardwire connection, a wireless connection, any combination of the Internet, local area network(s) such as an intranet, wide area network(s), cellular networks, Wi-Fi networks, and/or so on. The one or more sensors 12A, 12B, which may themselves include at least one processor and/or memory, may represent a set of arbitrary sensors, medical devices or other computing devices executing application(s) that respectively send data inputs to the one or more servers/computing devices and/or receive data outputs from the one or more servers/computing devices. Such servers/computing devices 24 may include, for example, one or more of desktop computers, laptops, mobile computing devices (e.g., tablets, smart phones, wearable devices), server computers, and/or so on. In certain implementations, the input data may include, for example, analog and/or digital signals.

Subject data from the subject 1 via the sensors 12A, 12B may be processed by the computing device 14 on the processor(s) 16 via a classification algorithm 100—such as a hybrid classification algorithm 100—where pupillary and non-pupillary responses are measured—comprising a plurality of optional steps. In various implementations, this processing via the computing device 14 and/or display 20 provides target selection, letter selection, confirmation of information, or icon selection, for example. The inclusion of pupil information is a technological improvement over the prior art as it may be used in single-trial selection paradigms and requires no initial operator or user training. In essence, providing an additional physiological signal with subject data that correlates with target selection is effective at reducing the decision manifold allowing for quicker and more accurate classifications.

In one step of an exemplary classification algorithm 100, and as shown in FIG. 1B, subject data is generated by being measured (box 102) via the one or more sensors 12A, 12B to be stored for further processing. In various implementations, for example, when utilizing a hybrid classification algorithm 100, the measured subject data (measured at box 102 via the first sensor 12A) can include data such as pupillary response or other eye behavior, such as pupil size, eye gaze dwell time, eye blink, eye movements, as well as other physiological responses to the cue (shown in FIG. 1A at reference number 2) from the other sensor 12B such as brain signal data as recorded by EEG, functional near infrared spectroscopy (fNIRS), electrocorticographraphy, ultrasound, or other peripheral physiological responses such as change in heart rate, motor evoked responses or galvanic skin response. Other examples are of course possible.

In a subsequent optional step, the subject data is digitized (box 104) via the computing device 14 and/or sensing device 12A, 12B for storage and processing, as would be understood. It is understood that in various implementations, the data is digitized as part of the hardware/software that is controlling the specific computing device, sensor or component.

In a subsequent optional step, the subject data is enhanced (box 106) via the computing device 14 and/or sensing device 12A, 12B. It is understood that various enhancements can be made, such as signal boosting and noise reduction, amongst others. For example, when measuring pupil size, one method of accounting for variable baseline pupil diameter between individuals can be addressed by subtracting a pre-trial baseline value (which may be the mean of several pre-trial samples), such that pupil size data is transformed into relative changes in pupil diameter, which standardizes the sample at (or near) zero at the onset of trials. This allows for detecting changes in pupil size as a function of different conditions (such as target symbol vs. nontarget symbol), and may account for differences in luminance conditions that naturally occur over time.

In a subsequent optional step, the subject data is grouped (box 108) via the computing device 14 and referenced to a common timing signal. For example, both pupil and EEG data may be grouped according to its proximity to presented targets as being within a window where features should be extracted.

In a subsequent optional step of the classification algorithm 100, a feature extraction algorithmic step (box 110) analyzes the incoming sample block from various modes of subject data—such as pupillary data and EEG data—independently to produce features that constitute corresponding feature vectors: such as a pupillary vector and an EEG vector. It is understood that the feature extraction algorithmic step can include a wide range of spatial, temporal, or spectral transformations depending on the specific application.

For example, in one exemplary process involving several sub-steps and as shown in FIG. 1C, the system 10 comprising a feature extraction algorithmic step 110 executes a computing (box 120) sub-step wherein the processor or computing devices computes the d-dimensional mean vectors for each of the classes of subject data (such as pupillary and EEG) from the collected and grouped dataset of subject data, so as to compare target vs. non-target responses and evaluate those subject data modes.

In another sub-step, the system 10 computes scatter matrices (box 122) for both the in-between-class and within-class subject data datasets.

In another sub-step, eigenvectors and the corresponding eigenvalues are computed (box 124) for the computed scatter matrices.

In another sub-step, the eigenvectors are sorted by decreasing eigenvalues (box 126), and (k) number of eigenvectors with the largest eignenvalues are chosen to form a d×k dimensional matrix.

In another sub-step, this matrix is used to transform samples (box 128) onto the newly created subspace via simple matrix multiplication to produce feature vectors separated by the linear discriminant classifier. It is fully appreciated that myriad alternate implementations are possible.

Returning to the implementation of FIG. 1B, in a subsequent optional step, the feature vector is translated via a translation algorithmic sub-step (box 112). It is appreciated that in various implementations, the translation algorithmic sub-step operates in concert with software designed to analyze such signals. For example, feature translation may use linear discriminant analysis to classify the selection of a target letter from a series of non-target letters for the various feature vectors. In certain of these implementations, a translation algorithmic sub-step translates the feature vector into device command(s) that carry out the intent or choice selection of the user, as would be appreciated by one of skill in the art.

In a subsequent optional step of the classification algorithm, the device responds to the command provided by the feature translation, with feedback of this selection being provided (box 114) to the user on the user interface running on a second personal computer, connected via TCP/IP protocols, or for example, via an operations system like the device 14—having a standard computer monitor display 20. Other operations systems such as in the video gaming or piloting applications, for example, would be readily apparent to those of skill in the art. In various implementations, software or firmware can be integrated to receive the feedback and provide commands to downstream devices and operations systems to perform commands, operate equipment or any of the other features or systems that require user input and would be appreciated by those of skill in the art.

Further discussion of each of these steps and sub-steps occurs below, in relation to the example of FIG. 2.

In various implementations, the disclosed AC systems 10, methods and devices make use of assistive communication technologies to improve system performance. Such assistive communication technologies include but are not limited to augmentative and alternative communication (AAC), including brain-computer interfaces (BCI), and can comprise electronic devices that utilize eye-tracking or camera technologies. To that end, it is understood that approaches these implementations can take/use assistive communication technologies such as BCI spellers and AAC technologies, some non-limiting examples including eye gaze devices by Tobii Dynavox such as PCEye Plus, I-12+, I-15+; LC Technologies products such as the Eyegaze Edge; PRC's NuEye® Tracking System; and Talk to Me Technologies eyespeak.

In various implementations, the assistive communication technology 12 is a BCI. BCIs enable communication between humans and machines by utilizing electrical or metabolic brain signals to classify user intent. Typically, these brain signals are recorded non-invasively either by electroencephalography (EEG), ultrasound, or functional near infrared spectroscopy (fNIRS), or invasively with electrocorticographic activity or single neuron activity as assessed by microelectrode arrays or glass cone electrodes. Hybrid brain computer interfaces typically combine two physiological signals to improve system communication speed and accuracy.

In various implementations, the system 10 uses an augmentative and alternative communication (AAC) as an input technology 12. In certain implementations, the AAC is a vision-controlled AAC, such as an eye gaze AAC similar to and including eye gaze devices by Tobii Dynavox such as PCEye Plus. I-12+, I-15+; LC Technologies such as the Eyegaze Edge; PRC's NuEye® Tracking System; and Talk to Me Technologies eyespeak.

Certain implementations of the AC system 10 relate to methods for improving the online classification performance of assistive communication technologies by using changes in the eye pupil features—such as size—as a physiological input. More specifically, pupil features could be used in isolation or in combination with another type of physiological input, such as other known ocular measures, peripheral physiological signals, or brain signals. That is, pupil features can be used in isolation or in combination with other features to reliably convey the user's intent for communication or target selection. Thus, in certain implementations, the use of eye pupil features can improve the performance of BCI and/or AAC assisted communication. Additional applications are of course possible.

While it is possible to use a fundamental signal feature, such as changes in pupil size or rate of change of pupil size within a specified window—for example one second following stimulus presentation—user intent may be more accurately represented through the use of more complex feature combinations. Thus, in certain embodiments of the AC system 10, pupil features are used that are linear or nonlinear combinations, ratios, statistical measures, or other transformations of multiple fundamental features detected at multiple time points; models such as artificial neural networks that do not model feature extraction or translation as distinct, cascaded stages may also be used. Further, both the user and the system may adapt so that the optimum classification algorithm at one time is different later. In various implementations, the system operation may depend on the interaction of the two for optimum performance. For the purpose of a BCI implementation, one such method is to combine pupil features with brain signal features using one of the specified complex feature combinations, in order to reflect the user's intent more accurately. The specific model utilized may be dependent on the BCI or AAC application, the user environment, as well as the user. Further implementations are of course possible.

Various implementations of the system 10 and associated devices and methods use eye pupil features as a physiological signal input to an assistive technology for the purposes of aided communication, such as with BCI or other AAC technologies. For example, pupil features can be used as part of a hybrid brain-computer interface that also uses brain signals to assist in classifying target versus non-target letters, words, or phrases for spelling. Pupil features could also be used as an input with AAC technology. For example, pupil size could be used to identify the user's intended picture, letters, words, or phrases with electronic devices that employ a camera or eye-tracking technology. Including pupil features as a physiological input with assistive technologies provides a number of advantages over similar systems/techniques known in the art, such as improved target detection, reduced errors, and the potential to assist individuals without volitional control over eye movement.

Certain embodiments herein relate to a process for utilizing eye pupil features in response to target letters, symbols, words, or phrases, for BCI or AAC assisted communication. Note that the user does not need to be able to perform any movement; just attending to a visual display with an intended target in mind is enough to induce a pupillary response.

Briefly, in accordance with one implementation, the process for pupillary response controlled functions is comprised of the steps of: non-invasively recording the pupil feature signal with known eye-tracking or camera technologies, such as the TOBII Pro TX300 remote eye-tracking system (Tobii Technology, Inc.) or SMI eye-tracking glasses (SensoMotoric Instruments, Teltow, Germany), processing the recording using signal conditioning software such as that provided with the open-source software BCI2000, or software developed with MATLAB (MathWorks, Inc.) or LabVIEW (National Instruments. Austin, Tex.), and transducing the signal into a functional command, such as target identification and user feedback) useful to the BCI or AAC application using classification algorithms, such as linear discriminant analysis, after training has been acquired.

Returning to the drawings, an exemplary implementation of a hybrid AC system 10 is set forth in FIG. 2 (below), according to one specific embodiment, in which a hybrid BCI combines pupillary response 12A and another sensing device, here an EEG 12B, using a hybrid pupil/P300 BCI speller classification algorithm, resulting in improved accuracy over known systems and methods. It is understood that the P300 BCI speller paradigm has been the benchmark for BCI applications, and utilizes brain signals as measured with electroencephalography (EEG) to evoke a P300 event-related potential (ERP) in response to visually displayed stimuli, such as letters. A P300 ERP is typically generated during an oddball paradigm in which a series of stimuli of two classes—target vs. non-target—are presented. The rarely presented target generates a peak approximately 300 ms after stimulus onset, which can be used to identify the intended letter for spelling, and thus communication. In this example, this system is used for assisted communication by combining subject data comprising brain signals (P300) as well as eye pupil features (pupillary response) in a hybrid classification algorithm. The output according to these implementations is letters used to spell words and sentences, though it is appreciated that a wide array of possible outputs are possible. For example, alternative outputs may include the selection of icons from a pictorial array, selecting between alternatives presented to an operator, or acknowledgement of error states presented. Data collection and signal classification can be performed by standard personal computers running specialized software designed for the capture and classification of signals used to control a remote computer, such as BCI2000, MATLAB, LabView and the like.

Figure 2:
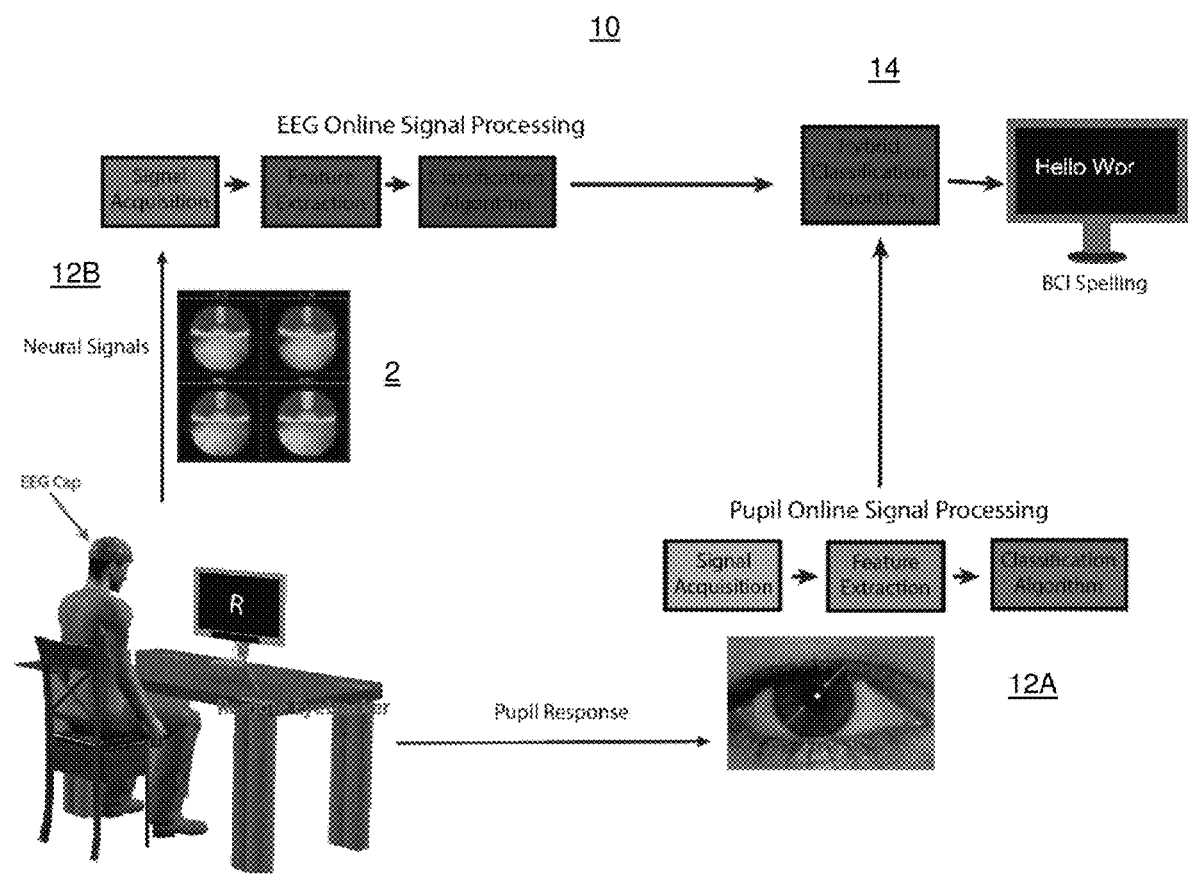
FIG. 2 is a pictorial representation of the hybrid pupil-EEG BCI speller device used as an exemplar system.

In this exemplary implementation of the AC system 10, the process of feature extraction and transduction using the system of FIG. 2 includes the pupillary response process steps in combination with the following steps:

In a first step, subject data is collected (box 102 in FIG. 1B) via sensing devices 12A, 12B, and in the case of electroencephalography are amplified at levels suitable for electronic processing, though the use of active or passive electroencephalography electrodes, such as the Biopac MP150. In this example, pupillary response is used as part of a hybrid brain-computer interface for assisted communication. Sensing device 12A represents pupil size, as recorded noninvasively with a pair of SMI eye-tracking glasses and iView ETG 2.2 experimental software (SensoMotoric Instruments, Teltow, Germany) with binocular tracking (sampling rate=30 Hz; gaze tracking range=800 horizontal, 600 vertical; accuracy=0.50; scene camera resolution=1280×960). Sensing device 12B represents electroencephalography (EEG) data. For recording and acquiring the electroencephalography (EEG) signal, BIOPAC MP150 (Biopac Systems, Inc, California, USA) data acquisition hardware and AcqKnowledge software were used.

The subject data are digitized (box 104 in FIG. 1B) and transmitted to a computer using digital acquisition devices such as a Biopac MP150. Signal conditioning acts to enhance (box 106 in FIG. 1B) the signal and remove extraneous information. Namely, the subject data were collected from nine channels (FZ, F3, F4, CZ, C3, C4, PZ, P3, and P4) following the international 10-20 montage for electrode placement. EEG activity was sampled at a frequency of 1000 Hz, and filtered online so that nonphysiological signals below about 0.1 Hz and above about 35 Hz were attenuated. Data were grounded by a midfrontal electrode, and all channels were referenced using the averaged mastoids technique. Letter stimuli were presented on a 45.5 cm [17.9 in] CRT monitor (Sony Trinitron Multiscan G400) running at 85 Hz re 1). Stimulus presentation and data acquisition were driven by a Hewlett Packard PC (Hewlett-Packard Development Co., Palo Alto, Calif.) with an Intel® Core™ i5-2400 CPU @ 3.10 GHz, 3101 MHz, 4 Core(s) processor and 64-bit Operating System. The monitor was placed along the midline of a large work surface, centered approximately 50 cm in front of the seated participant (visual angle of 39.96° horizontal and 30.88° vertical). A customized LabVIEW 12 (National Instruments, Austin, Tex.) program was used to control letter display to the screen, and to send a digital TTL signal from the PC presenting the stimuli to the Biopac MP150 to mark letter display events in the AcqKnowledge software recording. This customized software was used in conjunction with a NI LabVIEW Real-Time Module, which included a real-time operating system (OS) for more precise and predictable timing characteristics.

Subsequently, the digitized signals are grouped into sample blocks (box 108 in FIG. 1B), and a feature extraction algorithm (box 110 in FIG. 1B and in exemplary detail in FIG. 1C) is used to analyze the incoming sample block from pupil and brain independently to produce features that constitute the feature vector. In various implementations, the extracted features may include a wide range of spatial, temporal, or spectral transformations. The feature vector is passed to the feature translation stage (box 112 in FIG. 1B) in concert with software designed to analyze such signals, such as BCI2000, MATLAB, or LabView. The device command responds to the feature translation and feedback is provided (box 114 in FIG. 1B) to the user on the user interface running on a second personal computer, connected via TCP/IP protocols, for example, via a standard computer monitor.

Alternatively, for an AAC application, the process of extracting and transducing pupil features can be the same. Combining other ocular features (e.g., dwell time) can take place at the feature vector to feature translation stage (shown at box 112 in FIG. 1B), which can also be performed through LabView or MatLab software, for example.

Because the subject data features (brain signals, ocular measures, or peripheral signals) are indirect signals of user intent, in one embodiment, the algorithm, such as a linear discriminant analysis translates them into appropriate device commands for conveying the intended message. The translation algorithm (shown at box 112 in FIG. 1B) uses the set of features provided at a given instant as the input and processes the feature vector to output, compares that set of features to known training states, makes a state classification as to user intent, which the application device can recognize. The translation algorithm may be comprised of a mathematical equation, set of equations, or a mapping mechanism such as a lookup table. In its simplest form, a discriminant function (i.e., classification function) would translate the feature vectors into discrete categories of output. For example, the output of the model could be a translated command, such as a binary 0 or 1 that identifies a visually presented letter or symbol as a "target" or "non-target". It is readily appreciated that certain implementations can be supplemented via machine learning algorithms to improve classification accuracy.

Including pupil size as a physiological input to assistive technologies for aided communication has a number of benefits. One benefit is that this method could be employed with existing market technologies that have eye tracking or camera ability, such as those provided by Tobii Dynavox and Access Ingenuity, thus potentially improving the performance of these technologies without any additional hardware-associated expense. Further, as EEG becomes less expensive, this could become a commercial-off-the-shelf EEG-based BCI that provides a feasible and affordable solution for individuals with movement disorders. Such examples of low-cost EEG solutions are systems provided by EMOTIV technologies. In addition, new AAC or BCIs that utilize pupil features may be less expensive than eye tracking based technologies, as recording pupillometry does not require expensive eye-tracking technology, and may be possible with standard personal computer and laptop computer web cameras. Plus, AAC and BCIs that require eye movement are not usable for locked-in patients or in environments where eye-tracking is not feasible (such as in natural sunlight). This is important, as this one assistive technology could be used from early to late stage ALS, ensuring the patient does not need to switch technologies as their disease progresses. For example, those with spinal-onset ALS typically retain intelligible speech longer, but lose limb control first. These users would be able to employ the system to interface with a computer for written communication initially, and transition to speech output through synthesized speech when necessary. Those with bulbar-onset ALS typically experience speech and swallowing deficits first, but continue to walk, drive, write, and type for a period before losing motor control. These users would need to interface with the system for speech output, and would benefit from being able to make selections from the display with less effort, thereby preserving their energy.

Existing AAC systems use camera or eye-tracking technology to determine eye movements or gaze, but not changes in pupil features. According to certain specific embodiments herein, the process for the analysis and conversion of eye pupil features, such as size, can be used as part of a vision-controlled AAC to be used as an input for determining the user's intended target; pupil size can be combined with dwell time, eye blink, or other selection techniques to improve classification performance.

When a BCI utilizes more than one physiological input, it is referred to as a hybrid brain-computer interface. Hybrid BCIs may be composed of two signals recorded directly from the brain, or one brain signal and another system. Non-invasive hybrid BCIs for communication offer the potential of increased performance (i.e., classification accuracy) without an increase in clinical risk. In one embodiment, there is provided a process for the analysis and conversion of pupil features as part of a BCI to classify the user's intended target to assist with aided communication.

EXPERIMENTAL EXAMPLES

The following examples are put forth so as to provide those of ordinary skill in the art with a complete disclosure and description of how the articles, devices and/or methods claimed herein are made and evaluated, and are intended to be purely exemplary of the invention and are not intended to limit the scope of what the inventors regard as their invention. However, those of skill in the art should, in light of the present disclosure, appreciate that many changes can be made in the specific embodiments which are disclosed and still obtain a like or similar result without departing from the spirit and scope of the disclosure.

Participants.

Twenty-five healthy participants (n=25, Age range 21-57, 18 female) from the University of South Dakota participated in this experiment.

Procedure.

Participants were given a target letter, which would appear randomly within the stimulus set. Each letter was used as a target one time, resulting in 26 trials for each of 4 inter-stimulus presentation rates: 250 ms, 500 ms, 750 ms, and 1000 ms. NASA Task Load Index (NASA-TLX) was used to assess subjective workload after each presentation rate.

Results.

Figure 3:
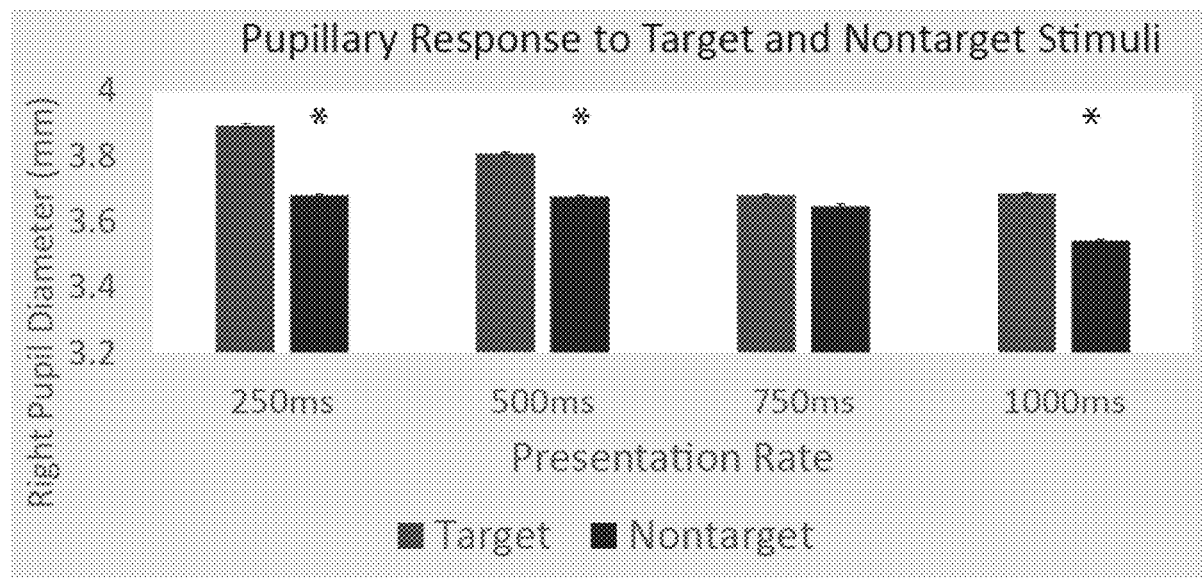
FIG. 3 shows the pupil diameter increase for target vs. nontarget letter stimuli. Pupil diameter was determined by finding the maximum difference between baseline (100 ms pre-stimulus) and post-stimulus (up to 1000 ms) for 26 target (grey) and 26 randomly selected non-target letters (blue) at each of the target stimuli presentation rates (250 ms, 500 ms, 750 ms, and 1000 ms). Pupil size increased for target vs. nontarget letter stimuli at each of the presentation rates (250 ms, 500 ms, 750 ms, and 1000 ms).

FIG. 3 shows the pupil diameter increase for target vs. nontarget letter stimuli. Pupil diameter was determined by finding the maximum difference between baseline (100 ms pre-stimulus) and post-stimulus (up to 1000 ms) for 26 target and 26 randomly selected non-target letters.

Figure 4:
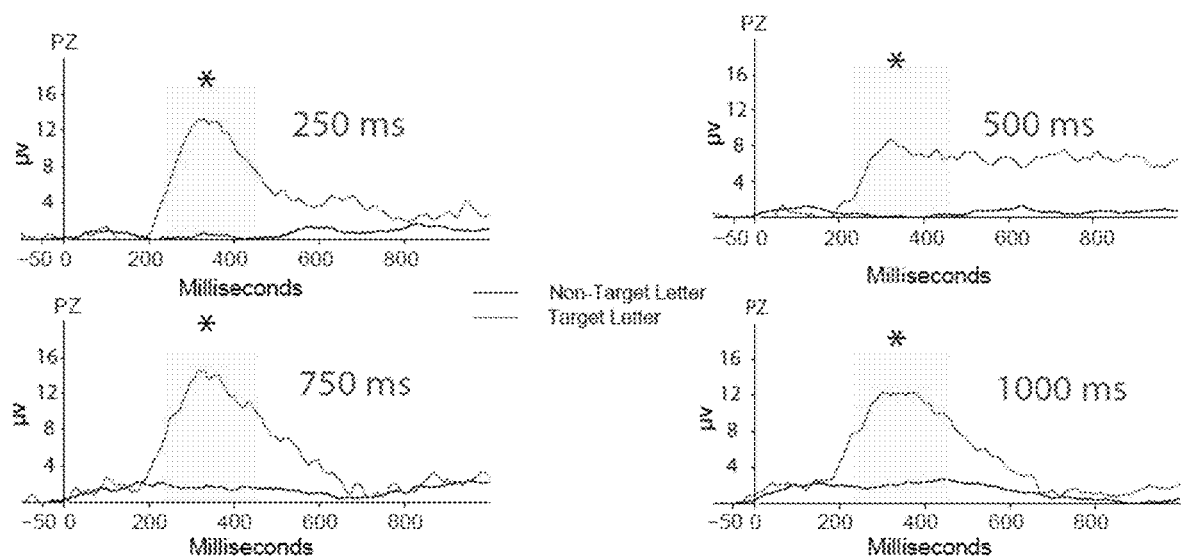
FIG. 4 shows average Event Related Potentials (ERPs). A prominent P300 ERP occurring around 250-450 ms can be identified in those trials in which a target stimulus was presented (red line) when compared to those trials in which a nontarget letter was presented (black line). As expected, the primary distribution of the P300 was in the centro-parietal regions of the scalp. P300 amplitude increased for target vs. nontarget letter stimuli at each of the stimuli presentation rates (250 ms, 500 ms, 750 ms, and 1000 ms).

FIG. 4 shows average ERPs. A prominent P300 occurring around 250-450 ms can be identified in those trials in which a target stimulus was presented (red line) when compared to those trials in which a distracter letter was presented (black line). As expected, the primary distribution of the P300 was in the centro-parietal regions of the scalp. P300 amplitude increase for target vs. nontarget letter stimuli at each of the target stimuli presentation rates (250 ms, 500 ms, 750 ms, and 1000 ms).

Figure 5:
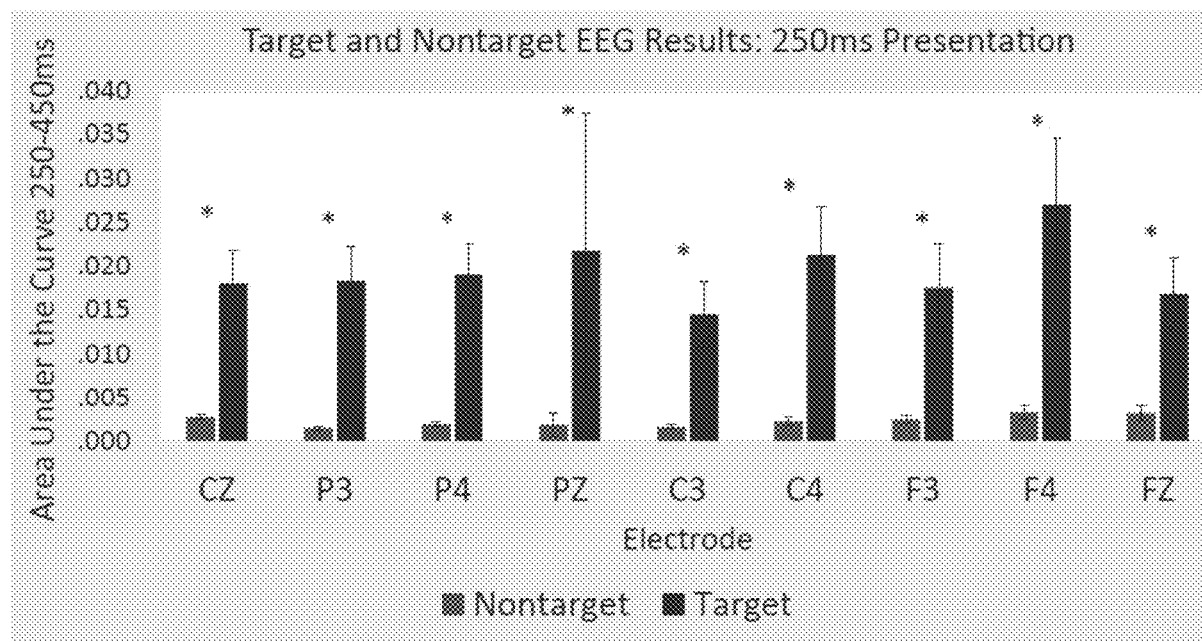
FIG. 5 shows EEG Measurements of the P300 across electrode sites for the 250 ms presentation rate. Areas under the curve were calculated for the 250 ms-450 ms timeframe following stimulus presentation. All electrode sites show a robust P300 following presentation of the target stimuli at the 250 ms presentation rate.

FIG. 5 shows EEG Measurements of the P300 across electrode sites for the 250 ms presentation rate. Areas under the curve were calculated for the 250 ms-450 ms timeframe following stimulus presentation. All electrode sites show a robust P300 following presentation of the target stimuli at the 250 ms presentation rate.

Figure 6:
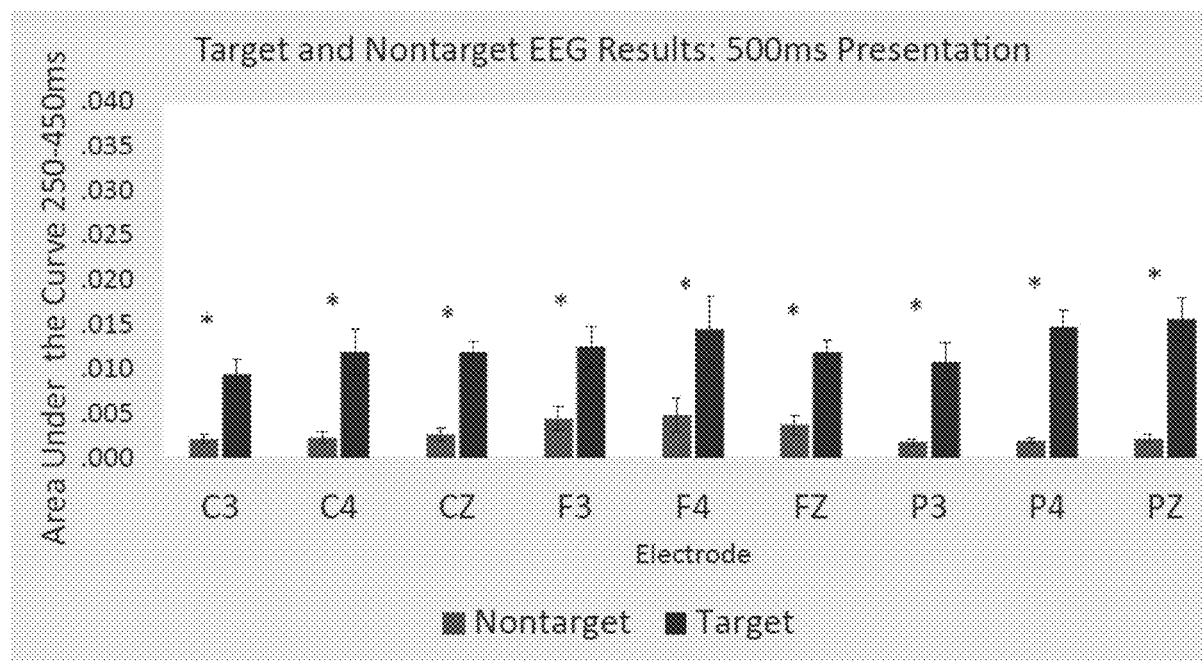
FIG. 6 shows EEG Measurements of the P300 across electrode sites for the 500 ms presentation rate. Areas under the curve were calculated for the 250 ms-450 ms timeframe following stimulus presentation. All electrode sites show a robust P300 following presentation of the target stimuli at the 500 ms presentation rate.

FIG. 6 shows EEG Measurements of the P300 across electrode sites for the 500 ms presentation rate. Areas under the curve were calculated for the 250 ms-450 ms timeframe following stimulus presentation. All electrode sites show a robust P300 following presentation of the target stimuli at the 500 ms presentation rate.

Figure 7:
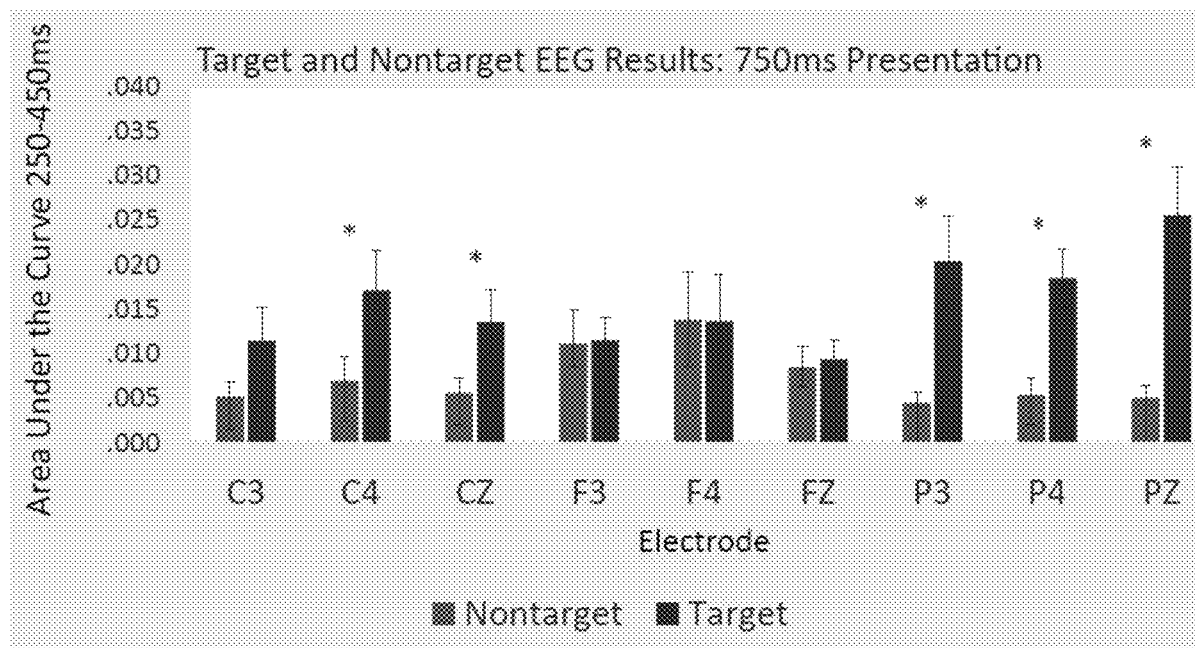
FIG. 7 shows EEG Measurements of the P300 across electrode sites for the 750 ms presentation rate. Areas under the curve were calculated for the 250 ms-450 ms timeframe following stimulus presentation. The majority of electrode sites (5/9) show a robust P300 following presentation of the target stimuli at the 750 ms presentation rate.

FIG. 7 shows EEG Measurements of the P300 across electrode sites for the 750 ms presentation rate. Areas under the curve were calculated for the 250 ms-450 ms timeframe following stimulus presentation. The majority of electrode sites (⅝) show a robust P300 following presentation of the target stimuli at the 750 ms presentation rate.

Figure 8:
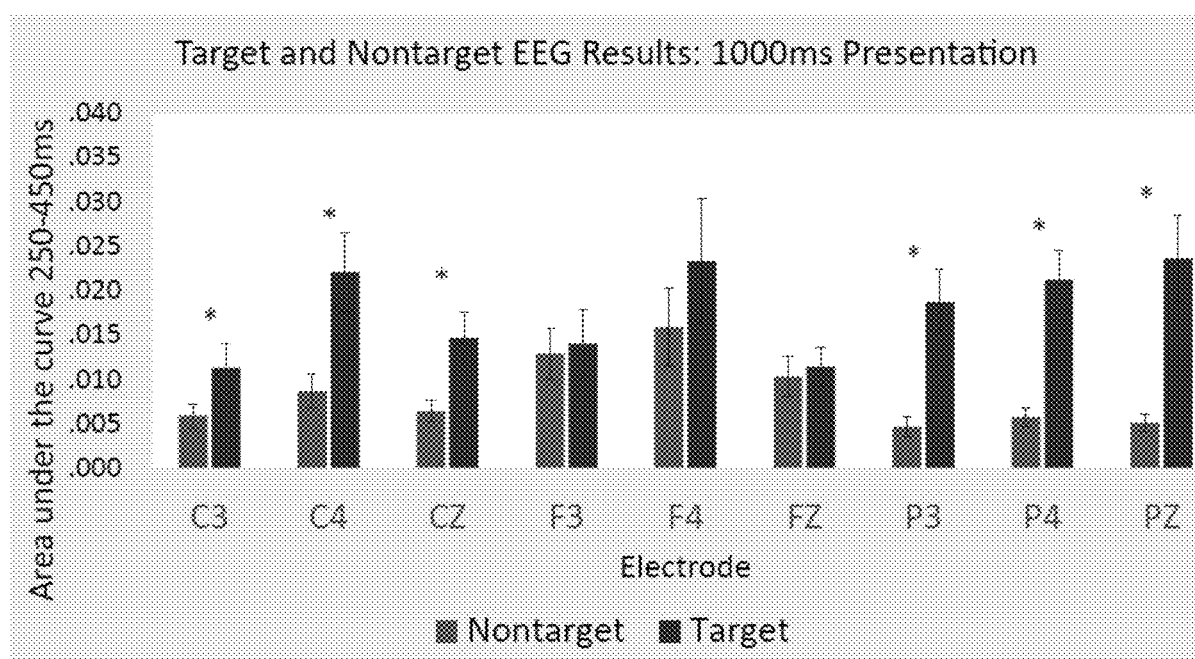
FIG. 8 shows EEG Measurements of the P300 across electrode sites for the 1000 ms presentation rate. Areas under the curve were calculated for the 250 ms-450 ms timeframe following stimulus presentation. The majority of electrode sites (6/9) show a robust P300 following presentation of the target stimuli at the 1000 ms presentation rate.

FIG. 8 shows EEG Measurements of the P300 across electrode sites for the 1000 ms presentation rate. Areas under the curve were calculated for the 250 ms-450 ms timeframe following stimulus presentation. The majority of electrode sites (⅝) show a robust P300 following presentation of the target stimuli at the 1000 ms presentation rate.

Tables 1-3 show classification accuracy for pupil diameter, P300 ERP, and hybrid pupil diameter+P300 ERP. BCILAB was used to test classifier accuracy for pupil diameter, P300, and the hybrid pupil+P300. Five classifiers were assessed for performance based on true negative and true positive rates. CSP was an effective classifier, and was used to calculate a sensitivity index (d').

Figure 9:
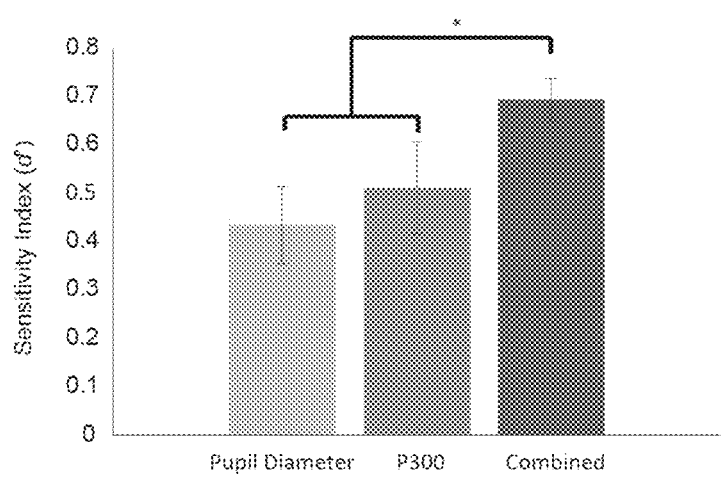
FIG. 9 is a bar graph showing sensitivity (d') for target letter classification performance using pupil diameter alone (yellow). P300 ERP alone (green), and the hybrid combination of pupil diameter and P300 ERP (blue). Multivariate test statistics demonstrated a significant main effect of classifier type [$F(2,8)=20.597$; Wilks $\lambda=0.163$; $p=0.001$]. Post-hoc tests revealed significant differences between the hybrid combination of pupil diameter/P300 ERP and each individual classifier ($P$'s$<0.05$).*Sample size N=11.

Due to violations of sphericity, multivariate test statistics were used. A significant main effect of classifier type was observed $[F(2,8)=20.597;$ Wilks $\lambda=0.163; p=0.001]$. Post-hoc tests revealed significant differences between the combined model and each individual classifier performance (P's<0.05), as is shown in FIG. 9.*Sample size N=11.

Figure 10:
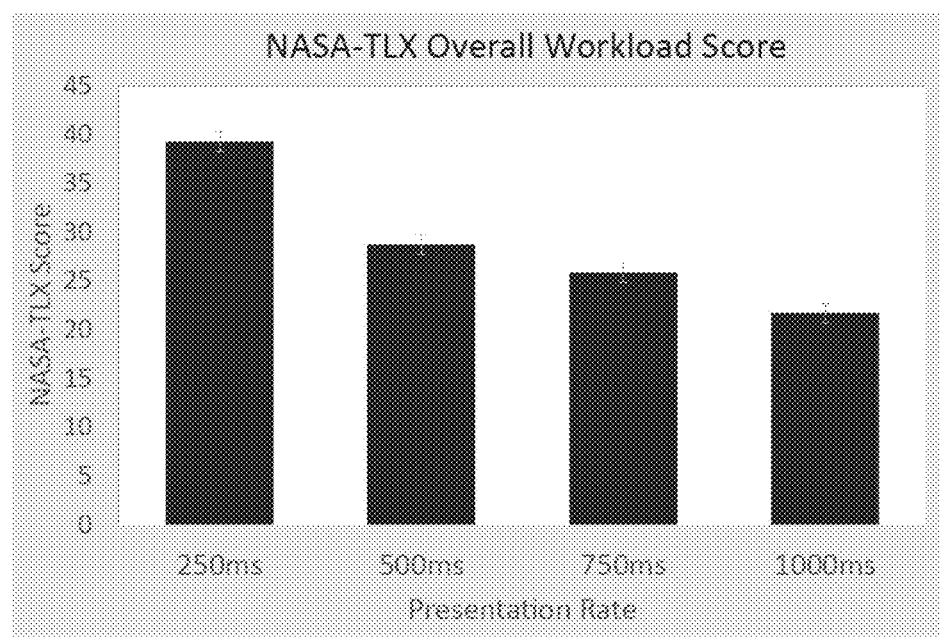
FIG. 10 shows the NASA Task Load Index (NASA-TLX) workload value differences based on rate of letter presentation. NASA-TLX was administered after each block of trials for each presentation rate (250 ms, 500 ms, 750 ms, 1000 ms) to assess subjective ratings of perceived workload. Results demonstrated that perceived workload increased with presentation rate, though classification performance based on sensitivity (d') did not [$F(3,7)=2.531$; Wilks $\lambda=0.480$; $p=0.141$].

FIG. 10 shows the NASA-TLX workload values differences based on rate of letter presentation.

The main effect of presentation rate was significant $[F(2.02, 48.46)=7.118, p=0.002]$. Mental demand and time pressure were highest in the 250 ms presentation condition.

In this example, pupil diameter increases as a function of target letter when using a single-letter presentation BCI format. A prominent P300 is observable at multiple electrode sites and at multiple presentation rates that would be suitable for use in single-letter presentation BCI applications. Classification accuracy is significantly improved through the use of a hybrid pupil/P300 classification algorithm. Subjective assessments of various presentation rates demonstrates increases in workload during faster presentation rates.

In summary, this example demonstrates the utility of combining pupil response in BCI systems as a readily available physiological measurement that increases classification performance above current BCI interfaces.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the term "subject" refers to the target of administration, e.g., an animal. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed systems and methods, the subject has been diagnosed with a need for treatment of one or more disorders.

Although the disclosure has been described with reference to preferred embodiments, persons skilled in the art will recognize that changes may be made in form and detail without departing from the spirit and scope of the disclosed apparatus, systems and methods.

What is claimed is:

1. A pupillary assisted communication system, comprising:
   a. a pupillary-response sensing device constructed and arranged to generate subject data;
   b. a non-pupillary response sensing device constructed and arranged to generate subject data;
   c. at least one computing device comprising a display, memory, and at least one processor constructed and arranged for executing a hybrid classification algorithm comprising a plurality of steps, comprising:
      i. grouping subject data from the pupillary-response and non-pupillary response sensing devices into sample blocks;
      ii. executing a feature extraction algorithmic step to produce at least one feature vector, the feature algorithmic step comprising:
         a vector computing sub-step;
         a scatter matrix computing sub-step; and
         an eigenvector and eigenvalue computing sub-step;
      iii. translating the feature vector; and
      iv. providing feedback via the at least one computing device display.

2. The system of claim 1, wherein the subject data comprises at least one response selected from the group consisting of pupil size, eye gaze dwell time, eye blink, eye movement, EEG, functional near infrared spectroscopy, electrocorticography, ultrasound, change in heart rate, motor evoked responses and galvanic skin responses.

3. The system of claim 1, wherein subject data is generated via BCI.

4. The system of claim 1, wherein the subject data is generated via augmentative and alternative communication.

5. The system of claim 1, further comprising an eigenvalue sorting sub-step.

6. The system of claim 5, wherein the plurality of sub-steps comprises a sample transforming step.

7. The system of claim 1, wherein the subject data comprises brain signal data.

8. The system of claim 1, wherein the subject data is generated via augmentative and alternative communication.

9. A pupillary assisted communication system, comprising:
   a. a pupillary-response sensing device constructed and arranged to generate subject data;
   b. a non-pupillary response sensing device constructed and arranged to generate subject data;
   c. at least one computing device constructed and arranged for executing a hybrid classification algorithm comprising a plurality of steps, comprising:
      grouping subject data from the pupillary-response and non-pupillary response sensing devices into sample blocks;
      executing a feature extraction algorithmic step to produce at least one feature vector, the feature algorithmic step comprising:
         a vector computing sub-step;
         a scatter matrix computing sub-step; and
         an eigenvector and eigenvalue computing sub-step; and
      translating the feature vector.

10. The system of claim 9, further comprising an eigenvalue sorting sub-step.

11. The system of claim 9, further comprising a sample transforming step.

12. The system of claim 9, wherein the subject data comprises at least one response selected from the group consisting of pupil size, eye gaze dwell time, eye blink, eye movement, EEG, functional near infrared spectroscopy, electrocorticography, ultrasound, change in heart rate, motor evoked responses and galvanic skin responses.

13. The system of claim 9, wherein subject data is generated via BCI.

14. The system of claim 9, wherein the subject data is generated via augmentative and alternative communication.

15. The system of claim 9, wherein the subject data comprises brain signal data.

16. The system of claim 15, further comprising an EEG.

17. The system of claim 9, further comprising a display constructed and arranged to provide the feedback.

18. The system of claim 9, wherein the pupillary-response sensing device is constructed and arranged to measure at least one response selected from the group consisting of pupil size, eye gaze dwell time, eye blink and eye movement.

19. A pupillary assisted communication system, comprising a computing device constructed and arranged for:
   a. receiving subject data generated from:
      i. a pupillary-response sensing device constructed and arranged to generate subject data; and
      ii. a non-pupillary response sensing device constructed and arranged to generate subject data; and
   b. executing a hybrid classification algorithm comprising a plurality of steps comprising:
      i. grouping subject data from the pupillary-response and non-pupillary response sensing devices into sample blocks;
      ii. executing a feature extraction algorithmic step to produce at least one feature vector, the feature algorithmic step comprising:
         A. a vector computing sub-step;
         B. a scatter matrix computing sub-step; and
         C. an eigenvector and eigenvalue computing sub-step; and
      iii. translating the feature vector.

20. The system of claim 19, wherein the subject data comprises at least one response selected from the group consisting of pupil size, eye gaze dwell time, eye blink, eye movement, EEG, functional near infrared spectroscopy, electrocorticography, ultrasound, change in heart rate, motor evoked responses and galvanic skin responses.

* * * * *